United States Patent
He et al.

(10) Patent No.: US 10,904,318 B2
(45) Date of Patent: Jan. 26, 2021

(54) IMAGING SYSTEM AND A COMMUNICATION PLATFORM FOR COMMUNICATION AMONG A PLURALITY OF NODES OF THE IMAGING SYSTEM

(71) Applicant: KONINKLIJKE PHILIPS N.V., Eindhoven (NL)

(72) Inventors: Bin He, Shenyang (CN); Minghui Jia, Shenyang (CN); Xuebing Zhou, Shenyang (CN); Junfeng Xi, Shenyang (CN); Huaizhi Wang, Shenyang (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 30 days.

(21) Appl. No.: 16/087,118

(22) PCT Filed: Mar. 27, 2017

(86) PCT No.: PCT/EP2017/057162
§ 371 (c)(1),
(2) Date: Sep. 21, 2018

(87) PCT Pub. No.: WO2017/167674
PCT Pub. Date: Oct. 5, 2017

(65) Prior Publication Data
US 2019/0098074 A1    Mar. 28, 2019

(30) Foreign Application Priority Data

Mar. 31, 2016  (WO) ................ PCT/CN2016/077979
Jun. 7, 2016  (EP) ..................................... 16173298

(51) Int. Cl.
*G06F 15/16*     (2006.01)
*H04L 29/08*     (2006.01)
(Continued)

(52) U.S. Cl.
CPC ............ *H04L 67/10* (2013.01); *G06F 19/321* (2013.01); *G16H 30/20* (2018.01); *G16H 30/40* (2018.01); *H04L 49/90* (2013.01)

(58) Field of Classification Search
CPC ..................................................... H04L 67/10
(Continued)

(56) References Cited

U.S. PATENT DOCUMENTS 5,764,955 A * 6/1998 Doolan ............... H04L 41/0213
709/223
9,092,282 B1 7/2015 Leonard
(Continued)

FOREIGN PATENT DOCUMENTS

WO  2012/073167  6/2012

OTHER PUBLICATIONS

Moon, et al., "Persistent Publish/Subscribe Messaging in Medical Devices" QNX Software Systems.

*Primary Examiner* — Hamza N Algibhah
(74) *Attorney, Agent, or Firm* — Larry Liberchuk

(57) ABSTRACT

The present invention proposes an imaging system and a communication platform for communication among a plurality of nodes of the imaging system. A node of the imaging system comprises a protocol module (510) for receiving a data message over the network; a network module (520) for receiving a data field of the data message from the protocol module; and at least one service module (530-1, . . . , 530-n); wherein the data field comprises a message identifier (MsgID) for indicating a type of the data message, and a payload field; each service module (530-1, . . . , 530-n) comprises at least one message handler (532) for handling a
(Continued)

payload of a data message; the network module (520) comprises a dispatcher (521), a plurality of queues (523), a call-back module (522), and a memory (524) for storing a first mapping between the message identifiers and the plurality of queues and a second mapping between the message identifiers (MsgID) and call-back handlers, wherein the dispatcher (521) is configured to dispatch the data message to one of the plurality of queues (523) based on the message identifier (MsgID) and the first mapping, and the call-back module (522) is configured to process a data message in each of the plurality of queues based on the second mapping, each call-back handler being directed to a message handler at a service module.

14 Claims, 10 Drawing Sheets

(51) Int. Cl.
*G06F 19/00* (2018.01)
*G16H 30/20* (2018.01)
*G16H 30/40* (2018.01)
*H04L 12/861* (2013.01)

(58) Field of Classification Search
USPC .......................................................... 709/203
See application file for complete search history.

(56) References Cited

U.S. PATENT DOCUMENTS

| | | | |
|---|---|---|---|
| 10,084,719 B2* | 9/2018 | Hussain | H04L 47/6215 |
| 2004/0122906 A1 | 6/2004 | Goodman | |
| 2005/0232291 A1 | 10/2005 | Brown | |
| 2007/0268903 A1* | 11/2007 | Nakagawa | H04L 47/2408 |
| | | | 370/392 |
| 2008/0059597 A1 | 3/2008 | Blevins | |
| 2009/0036750 A1 | 2/2009 | Weinstein | |
| 2009/0316714 A1* | 12/2009 | Kodaka | H04L 47/2408 |
| | | | 370/412 |
| 2011/0235630 A1* | 9/2011 | Hui | H04L 47/52 |
| | | | 370/352 |
| 2011/0258628 A1* | 10/2011 | Devadhar | G06F 9/546 |
| | | | 718/100 |
| 2012/0243410 A1* | 9/2012 | Vedula | H04L 41/5025 |
| | | | 370/235 |
| 2013/0173719 A1 | 7/2013 | Ahmed | |
| 2013/0318178 A1* | 11/2013 | Addante | G06Q 10/107 |
| | | | 709/206 |
| 2014/0177935 A1* | 6/2014 | Nair | A61B 8/06 |
| | | | 382/132 |
| 2015/0067021 A1 | 3/2015 | Protas | |
| 2015/0100787 A1* | 4/2015 | Westin | G06F 21/602 |
| | | | 713/168 |
| 2015/0138977 A1* | 5/2015 | Dacosta | H04W 28/021 |
| | | | 370/235 |
| 2016/0182380 A1* | 6/2016 | Mehra | H04L 45/7453 |
| | | | 709/226 |
| 2016/0226797 A1* | 8/2016 | Aravinthan | H04L 49/251 |
| 2017/0244637 A1* | 8/2017 | Singhal | H04L 45/7453 |

\* cited by examiner

US 10,904,318 B2

IMAGING SYSTEM AND A COMMUNICATION PLATFORM FOR COMMUNICATION AMONG A PLURALITY OF NODES OF THE IMAGING SYSTEM

CROSS REFERENCE TO RELATED APPLICATIONS

This application is the U.S. National Phase application under 35 U.S.C. § 371 of International Application No. PCT/EP2017/057162, filed Mar. 27, 2017, published as WO 2017/167674 on Oct. 5, 2017, which claims the benefit of European Patent Application Number 16173298.7 filed Jun. 7, 2016 and Chinese Patent Application Number PCT/CN2016/077979 filed Mar. 31, 2016. These applications are hereby incorporated by reference herein.

FIELD OF THE INVENTION

The present invention generally relates to an imaging system such as a medical imaging system, and more particularly to a communication platform for communication among a plurality of nodes in the imaging system, and is described with particular application to computed tomography (CT); however, the following is also amenable to other imaging systems such as MRI (Magnetic Resonance Imaging), PET (Positron Emission Tomography), PET-CT, etc.

BACKGROUND OF THE INVENTION

FIG. 1 shows a conventional imaging system such as a CT imaging system 100 as described in WO2012/073167. The imaging system 100 includes a stationary gantry 102 and a rotating gantry 104, which is rotatably supported by the stationary gantry 102. The rotating gantry 104 rotates around an examination region 106 about a longitudinal or z-axis. A support 108, such as a couch, supports a subject in the examination region 106 and can be used to position the subject with respect to x, y, and/or z axes before, during and/or after scanning. A radiation source 110, such as an x-ray tube, is supported by the rotating gantry 104 and rotates along with the rotating gantry 104 about the examination region 106, and emits radiation that traverses the examination region 106. A source collimator 112 collimates the emitted radiation to produce a generally fan, wedge, or cone shaped radiation beam that traverses the examination region 106. A radiation sensitive detector array 114, located opposite the radiation source 110 across the examination region 106, includes a plurality of detector pixels that detect radiation traversing the examination region 106 and generate projection data indicative thereof. A reconstructor 116 reconstructs the projection data and generates volumetric image data indicative of the examination region 106. An image processor 118 processes the volumetric image data and generates one or more images indicative of the detected radiation. A display 120 is utilized to present the one or more images. A general purpose computing system serves as an operator console 122, and includes an output device such as a display and an input device such as a keyboard, mouse, and/or the like. Software resident on the console 122 allows the operator to control the operation of the system 100, including controlling the clinical workflow. A control system serves as a gantry host 124, and is typically deployed inside the stationary gantry 102. The gantry host 124 provides control for various components, including controlling the movement of the support 108, controlling the scan flow such as the rotation of the rotating gantry 104, etc.

Recently, more components, such as various flat panels, have been proposed to be introduced into the imaging system. FIG. 2 shows an imaging system 200 such as a CT imaging system. As compared to the imaging system 100 of FIG. 1, the imaging system 200 further comprises a left panel 210, a right panel 210, and a CT box 230, in addition to the console 210 and the gantry host 220. Software resident on those components 210-230 may allow the operator to control the operation of the system 100. Each component may have its own operation system (OS), which may be different from each other and may be different from the OS of the console 210 (such as Microsoft Windows) and the OS of the gantry host 220 (such as Linux). For example, the OS of the flat panel can be android, iOS, Linux and Microsoft Windows etc.

US2005/0232291A1 discloses a method for validating messages in a message queuing software environment before the messages are transmitted to the recipient programs comprising a Message Validating Program.

U.S. Pat. No. 9,092,282B1 discloses a method for monitoring channels running on a queue manager. Both the total number of channel instances and instances of each named channel running on a queue manager may be monitored over time.

SUMMARY OF THE INVENTION

Referring to FIG. 2, in order to enable communication among a plurality of nodes of the imaging system 200, such as the console 210, the gantry host 220 and the various nodes 230-250, a communication network may be deployed to interconnect all these nodes. Since each of the plurality of nodes has its own OS, which may be different from that of other nodes, a possible solution can be to create more socket connections at the network layer, for example one socket connection for each pair of nodes to enable communication between them. However, the inventors of the present invention have recognized that such a solution, as illustrated in FIG. 9, has many disadvantages.

Each node comprises a network module 920 at a network layer and one or more service modules 930-1, 930-2 at a service layer above the network layer. Send/receive queues shall be implemented at each of the network layer and the service layer, including queue 923 at the network module 920 and queue 933 at each service module 930-1, 930-2. Usually, more than one thread is used to handle different types of messages for high performance or different types of service module. Each service module 930-1, 930-2 may comprise several message handlers and different message handlers will handle different types of data messages. The type of service modules may be not the same for different operation systems, and thus the source code cannot be reused.

The dispatcher is also relatively simple. One thread is used to receive all types of messages. One switch 921 at the network layer is needed to dispatch messages to different service modules of the service layer, and another switch 932 is also needed for each service module to parse the messages of interest one after another. It is not so real-time and cannot achieve high performance. And the service layer has to create and manage a message data cache/queue, a thread, and cannot focus on its own task such as processing the messages of interest. If a new type of data message is introduced to the imaging system 200, the source codes corresponding to service module 930-1, 930-2 need to be modified for each service module. If there are more than one nodes such as nodes 210-250 as shown in FIG. 2, modification will be needed for the source codes corresponding to all the service modules of all the nodes 210-250.

Therefore, it would be advantageous to provide an improved communication platform or architecture for communication among a plurality of nodes in the imaging system.

In accordance with an embodiment of a first aspect of the present invention, a node of a plurality of nodes in an imaging system is proposed. The imaging system comprises a network for communication among the plurality of nodes in the imaging system. The node comprises: a protocol module for receiving a data message over the network; a network module for receiving a data field of the data message from the protocol module; and at least one service module; wherein the data field comprises a message identifier for indicating a type of the data message, and a payload field; each service module comprises at least one message handler for handling a payload of a data message; the network module comprises a dispatcher, a plurality of queues, a call-back module, and a memory for storing a first mapping between the message identifiers and the plurality of queues and a second mapping between the message identifiers and call-back handlers, the dispatcher is configured to dispatch the data message to one of the plurality of queues based on the message identifier and the first mapping, and the call-back module is configured to process a data message in each of the plurality of queues based on the second mapping, each call-back handler being directed to a message handler at a service module.

In accordance with the aforementioned possible solution in FIG. 9, once it has received a message, the dispatcher of the network module is configured to check the type of the message, and it determines whether it is of interest for each service module of one or more service modules 930-1, 930-2 at the service layer, and dispatches the message to the service module if the message is of interest for a service module. Typically, at the network layer, a queue 923-1, 923-2 is created for each service module 930-1, 930-2, and the messages of interest for one service module are pushed into the same queue, and are to be pulled into a receiving queue 933 by the service module at the service layer; then, at each service module 930-1, 930-2 of the service layer, a dispatcher is configured to parse the messages in the receiving queue 933 one after another.

In the proposed solution, the messages are dispatched in a completely different way at the network layer, and no queue described as above or data cache is needed at the service layer. Each queue of the plurality of queues at the network layer is not dedicated to a certain service module, but rather, each queue is associated with one or more types of data message. The dispatcher of the network module is configured to dispatch the data message to one of the plurality of queues based on a mapping between the types of the data message and the plurality of queues. In an embodiment, all types of data messages can be dispatched to different queues depending on their scheduling strategies. For example, the types of data messages to be handled in series can be dispatched to one queue, and the types of data messages to be handled in parallel can be dispatched to another queue. In another embodiment, all types of data messages can be dispatched to different queues depending on latency requirements. For example, the types of data messages to be handled with little to no delay can be dispatched to one queue, and the types of data messages having more delay tolerance can be dispatched to another queue.

Furthermore, the proposed network module does not simply pass the data messages to the service layer, but the call-back module can directly provide a call-back handler, such as an enter address of a message handler at the service layer, for each data message based on a mapping between the message identifiers and the call-back handlers. Thus, there is no need to queue any data message at the service layer, and the network module is able to directly deliver the data message to the corresponding message handler at the service layer.

If a new type of data message is introduced to the imaging system 200, the massive source codes modification work used to be required for all of the switchers 932 and queues 933 of all the service modules of all the nodes are not needed any more because the work used to be done by the switchers 932 and queues 933 at the service layer is done by the network layer now. There is no need to modify the source codes at the network layer except for the very simple configuration modification of the first mapping and the second mapping by adding the relevant mapping for the new type of data message. Therefore, the imaging system 200 can be easily extended when new type of data message is introduced due to new application/service or new node introduced.

The first mapping and the second mapping can be pre-configured or dynamically configured.

In accordance with another embodiment of the present invention, the network module further comprises a register configured to receive, from a service module, a message identifier, a queue identity value for indicating one of the plurality of queues to which the data message with the message identifier is to be dispatched and a call-back handler directed to a message handler of the service module for handling the data message with the message identifier, and to update the first mapping and the second mapping based on the received message identifier (MsgID), the received queue identity value, and the received call-back handler.

In this way, even though not every service module manages to establish connections to other nodes, or to handle the queuing, it is still able to flexibly set or configure how its messages of interest shall be queued by informing the network module to which queue each type of data message shall be routed or dispatched, and furthermore, it is also able to flexibly configure the message handler for each of its messages of interest by setting the call-back handler. Consequently, all kinds of services could be deployed into the network easily. A client does not need to create the connection to a server of interest, and does not need to handle the sending and/or receiving of any data message; the client only needs to register its call-back for the message of interest, and to set how its messages of interest shall be queued. For example, the client can, by assigning its messages of interest to one or more of the plurality of queues, customize which type of message is to be handled in series, which type of message is to be handled in parallel, or which type of message is to be handled in a dedicated, non-shared queue.

In accordance with another embodiment of the present invention, the service module is further configured to generate a message identifier, a queue identity value for indicating one of the plurality of queues to which the data message with the message identifier is to be dispatched, and a call-back handler directed to a message handler of the service module for handling the data message with the message identifier based on configuration data.

In accordance with another embodiment of the present invention, the network module further comprises an unregister configured to receive, for a service module (530-1, . . . , 530-n) a message identifier, and to update the first mapping and the second mapping based on the received message identifier by removing the mapping corresponding to the received message identifier.

In case that a type of message is not of interest anymore for a service module, the service module can unregister this type of message by sending its message identifier to the unregister of the network module. Thus, the service module can dynamically configure the types of messages of interest.

In accordance with another embodiment of the present invention, the plurality of queues comprise a first queue and a second queue, and the number of threads assigned to the first queue is different from the number of threads assigned to the second queue. For example, the first queue can be assigned with a single thread to enable synchronous handling of messages therein, whilst the second queue can be assigned with more threads to enable higher throughput.

In some embodiments, the service module is further configured to send, to the network module, a value for indicating a number of threads assigned to a queue of the plurality of queues.

In this way, even though the queuing of the data messages is not carried out by each service module itself, the service module is still able to configure the number of threads for a queue at the network module so as to customize the processing performance of data messages in the queue. For example, the service module can customize which types of data message are to be handled by a single thread of the thread pool, or are to be handled by a thread shared with some other types of data message.

Different types of data messages may be handled in different scheduling strategies. For example, with respect to some types of data messages for carrying position feedback, only the last message needs to be handled whilst the previous ones can be dropped, but for some other types of data messages, such as data messages for carrying vital signals such as the ECG signal, no data message is dropped. By means of creating a first queue and a second queue with different scheduling strategies, data messages requiring different scheduling strategies can be handled properly in separate queues and will not influence each other.

In accordance with another embodiment of the present invention, one or more message identifiers are mapped to one of the plurality of queues.

In this way, there is no need to create one queue for each type of data message, but a selected set of types of data messages can share the same queue.

In accordance with another embodiment of the present invention, the network module is configured to send, to the protocol module, a data field and a node identifier, the node identifier indicating one or more nodes to which the data field is sent; and the protocol module is configured to generate a data message based on the data field and the node identifier.

In this way, the sending of data messages at the network layer is designed to be node-oriented, rather than connection-oriented. Conventionally, the sending of data messages at the network layer is connection-oriented. That is, a connection is established between each pair of service modules, and multiple connections are established at the network layer between each pair of nodes. Consequently, many data messages are synchronized unnecessarily. In the proposed solution, the sending of data messages at the network layer is node-oriented. Thus, the complexity of connection is hidden from the caller.

In accordance with another embodiment of the present invention, the plurality of nodes comprise a master node and at least one slave node; the protocol module of the node comprises a connection module and a memory; the memory of the master node is configured to store connection information of one or more nodes; the connection information of a node comprises the node identifier, the node address, and the connection status of the node; the connection module of the master node is configured to receive, from a node, a connection control message, the connection control message comprising: a node address of the node, the node address being unique in the network and being dynamically defined; a node identifier of the node, the node identifier being unique in the network; the connection module of the master node is further configured to update the connection information based on the received connection control message, and to send out a connection table based on the connection information, the connection table indicating a mapping between the node identifier and the node address.

In some embodiments, the connection module of a slave node is configured to send a connection control message; the connection module of the slave node is further configured to receive, from the master node, the connection table, and to establish a connection to each of one or more nodes based on the connection table.

In this way, the connections among the plurality of nodes can be established without pre-fixing the node identifier and/or node address for each node. Thus, adding and/or removal of individual nodes can be flexible, and the node address can be dynamically configured.

In one example, the master node is a gantry host. In an imaging system such as a CT system or PET-CT system, the gantry host is indispensable, and is thus suitable for serving as master node. In other imaging systems where there is no gantry host or the gantry host is dispensable, another node can be selected to serve as the master node. For example, in an MRI system, a controller for the gradient amplifier and/or the RF amplifier can be selected to serve as the master node.

In accordance with another embodiment of the present invention, the protocol module of the master node further comprises a disconnection event handling module; the connection module of the master node is further configured to generate a disconnection event when a connection status of a node becomes disconnected based on the stored connection information, and to send the disconnection event to the disconnection event handling module; the memory of the master node is further configured to store a third mapping between the disconnection event and the at least one operation; and the disconnection event handling module is configured to receive a disconnection event and to perform at least one operation in response to the disconnection event based on the third mapping.

In this way, the master node can monitor the connection status of all other nodes, and can take necessary actions against connection failure. For example, when a connection failure occurs during the running of a movement command for example for moving the support, such movement is stopped immediately to avoid any risk or danger which may be caused by the movement.

In accordance with another embodiment of the present invention, the protocol module (510-M, 510-S) is cross-platform. That is, the protocol module is applicable across various platforms, including Android, iOS, Linux, Microsoft Windows, etc. For example, the protocol module can be based on ZeroMQ and Protocol Buffer (PB) provided by Google. In other words, the protocol module is configured to perform communication over a heterogeneous network.

In accordance with an embodiment of a second aspect of the present invention, an imaging system is proposed, which comprises a plurality of aforementioned nodes, and a network for communication among the plurality of nodes.

In accordance with an embodiment of a third aspect of the present invention, a computer product is proposed comprising computer program instructions which, when being executed, perform a method of communication among a plurality of nodes in an imaging system over a network. The method comprises: at a protocol layer, receiving a data message over the network; at a network layer, receiving a data field of the data message from the protocol module (520), the data field comprising a message identifier (MsgID) for indicating the type of message, and a payload field; dispatching the data message to one of a plurality of queues based on the message identifier (MsgID) and a first mapping between the message identifiers and the plurality of queues; processing a data message in each of the plurality of queues based on a second mapping between the message identifier (MsgID) and a call-back handler, each call-back handler being directed to a message handler at a service layer for handling the payload of the data message; and at the service layer, handling the payload of the data message.

Other objects and advantages of the present invention will become more apparent and can be easily understood with reference to the description made in combination with the accompanying drawings.

DESCRIPTION OF THE DRAWINGS

The present invention will be described and explained hereinafter in more detail in combination with embodiments and with reference to the drawings, wherein.

Figure 1:
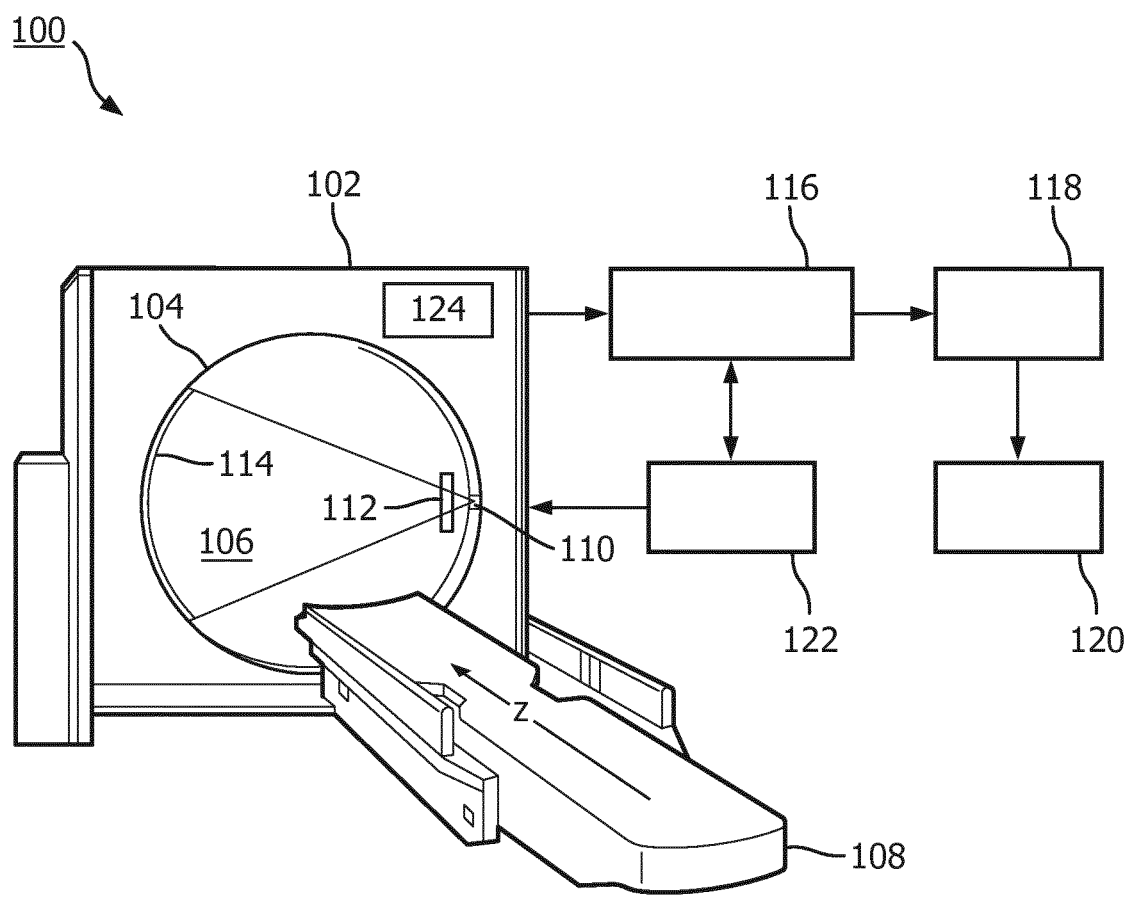
FIG. 1 illustrates a conventional imaging system such as a CT imaging system.
Figure 2:
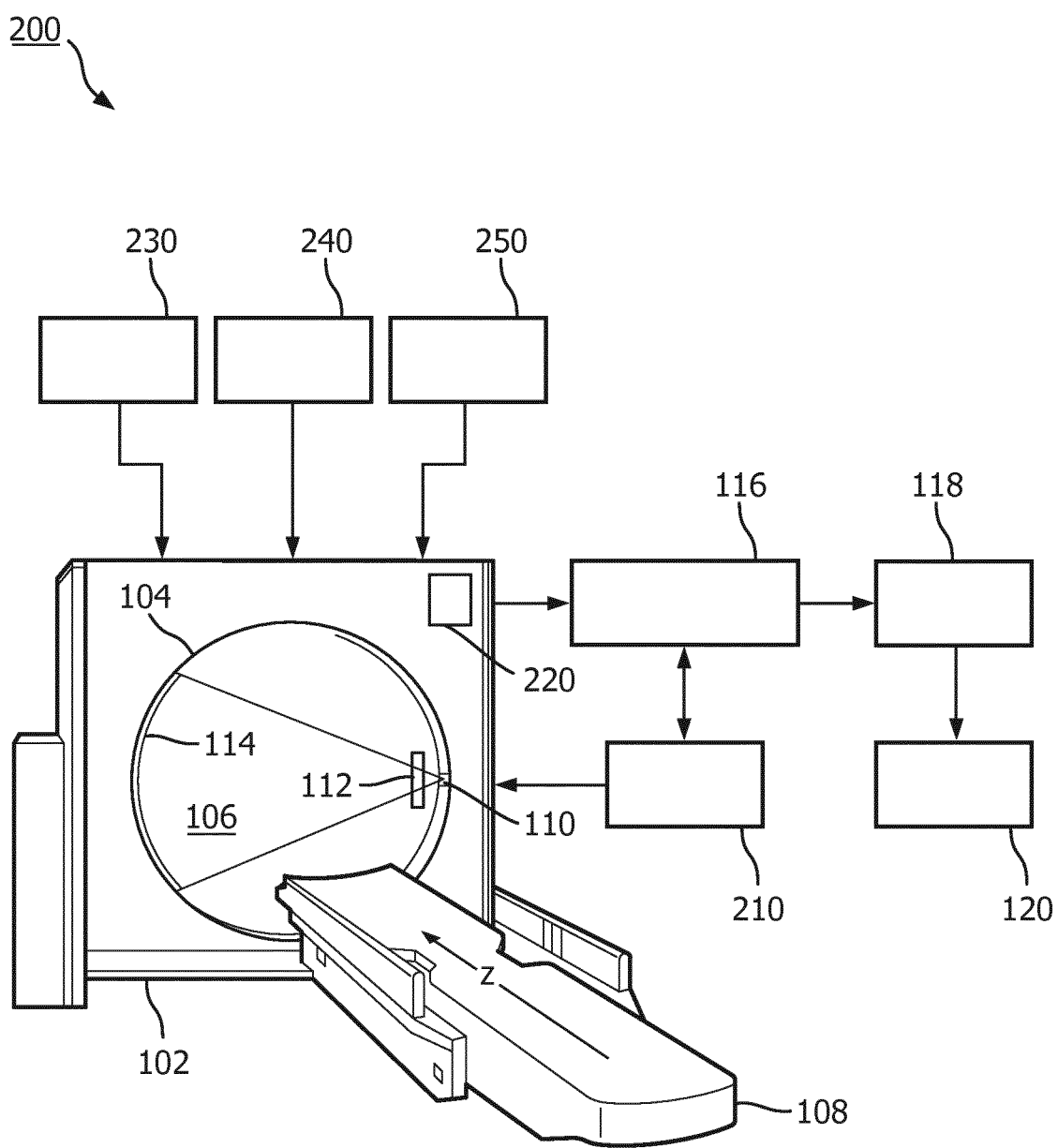
FIG. 2 illustrates an exemplary imaging system such as a CT imaging system in accordance with an embodiment of the present invention.

The same reference signs in the figures indicate similar or corresponding features and/or functionalities.

DETAILED DESCRIPTION

The present invention will be described with respect to particular embodiments and with reference to certain drawings, but the invention is not limited thereto but only by the claims. The drawings described are only schematic and are non-limiting. In the drawings, the size of some of the elements may be exaggerated and not drawn to scale for illustrative purposes.

Figure 3:
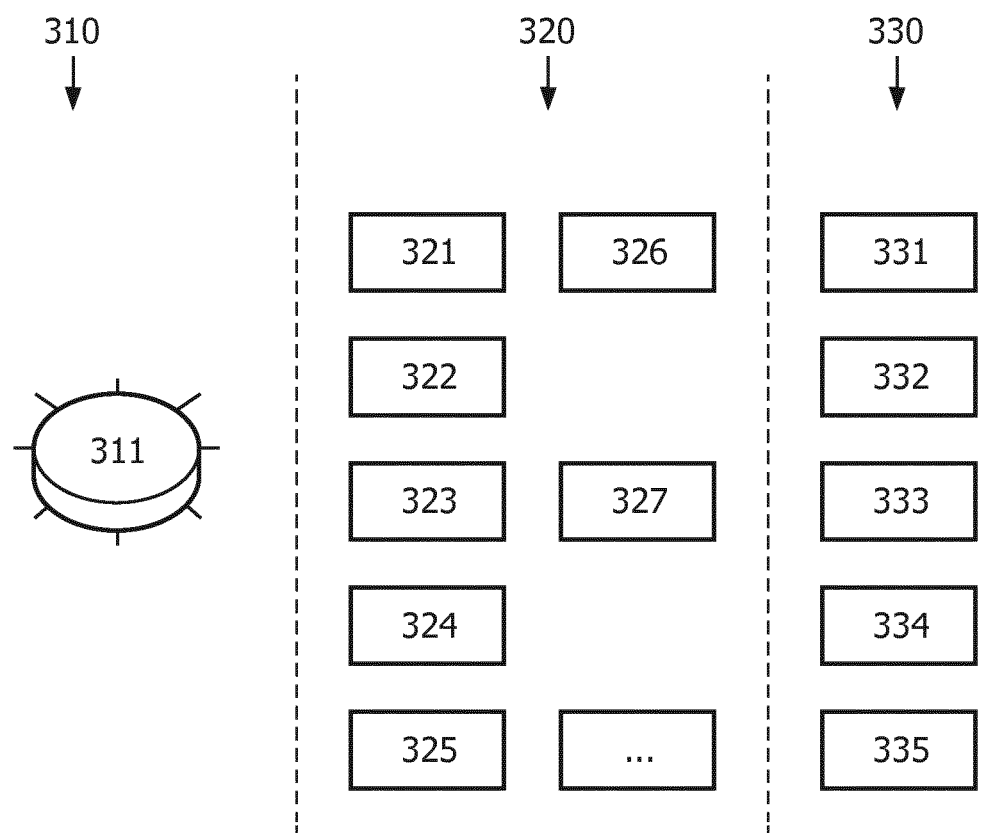
FIG. 3 illustrates an exemplary software architecture for the communication among a plurality of nodes of an imaging system in accordance with an embodiment of the present invention.

FIG. 3 illustrates an exemplary architecture for the communication among a plurality of nodes of an imaging system in accordance with an embodiment of the present invention. Referring to FIG. 3, the architecture comprises a communication basis 310, serving as the basis of the communication among the plurality of nodes. The communication basis is responsible for connecting nodes, sending, receiving and dispatching messages. The communication basis 310 can comprise a wired or wireless network. The communication basis 310 can comprise a heterogeneous network 311. A heterogeneous network is defined as a network connecting computers or other devices with different operation systems, different protocols and/or different access technologies. The architecture comprises a plurality of service providers 320, which are responsible for providing services for applications residing in various nodes. For example, the plurality of service providers 320 can comprise one or more of Session Manager 321, IMovement 322 for movement, IBL 323 for beam limiting, IWorkflow 324 for work flow, Virtual components 325, Hardware upgrade 326, other connection points 327, etc. The architecture further comprises a plurality of applications 330, each running at a certain node for providing services and/or serving as a user interface for accessing services. The plurality of applications 330 can comprise one or more of a console 331, a gantry host 332, and various panels such as a left panel 333, a right panel 334, and a CT box 335. For example, the console 331 can provide services such as IWorkflow 324; the gantry host 332 can provide movement services such as IMovement 323 and IBL 325; the left panel 331 and the right panel 332 allow operators to access services such as those provided by the console 331 and the gantry host 332. The plurality of applications 330 can be based on different operation systems, such as android, iOS, Linux and Microsoft Windows. In some imaging systems such as a CT system, the gantry host 332 is indispensable, whilst the other applications 330, such as left panel 333, right panel 334 are optional.

Figure 4:
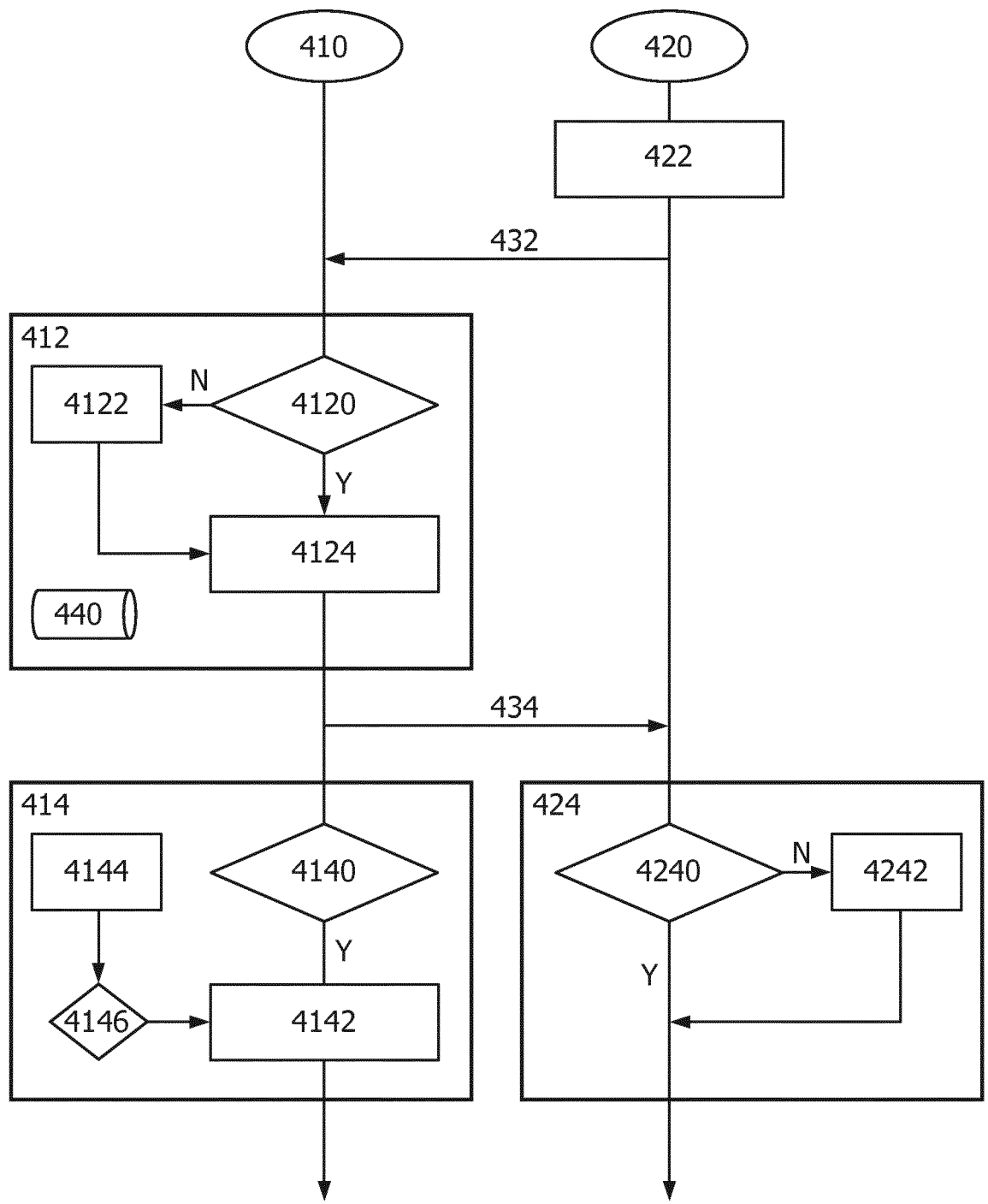
FIG. 4 illustrates an exemplary flow of establishing connections at the protocol layer in accordance with an embodiment of the present invention.
Figure 5:
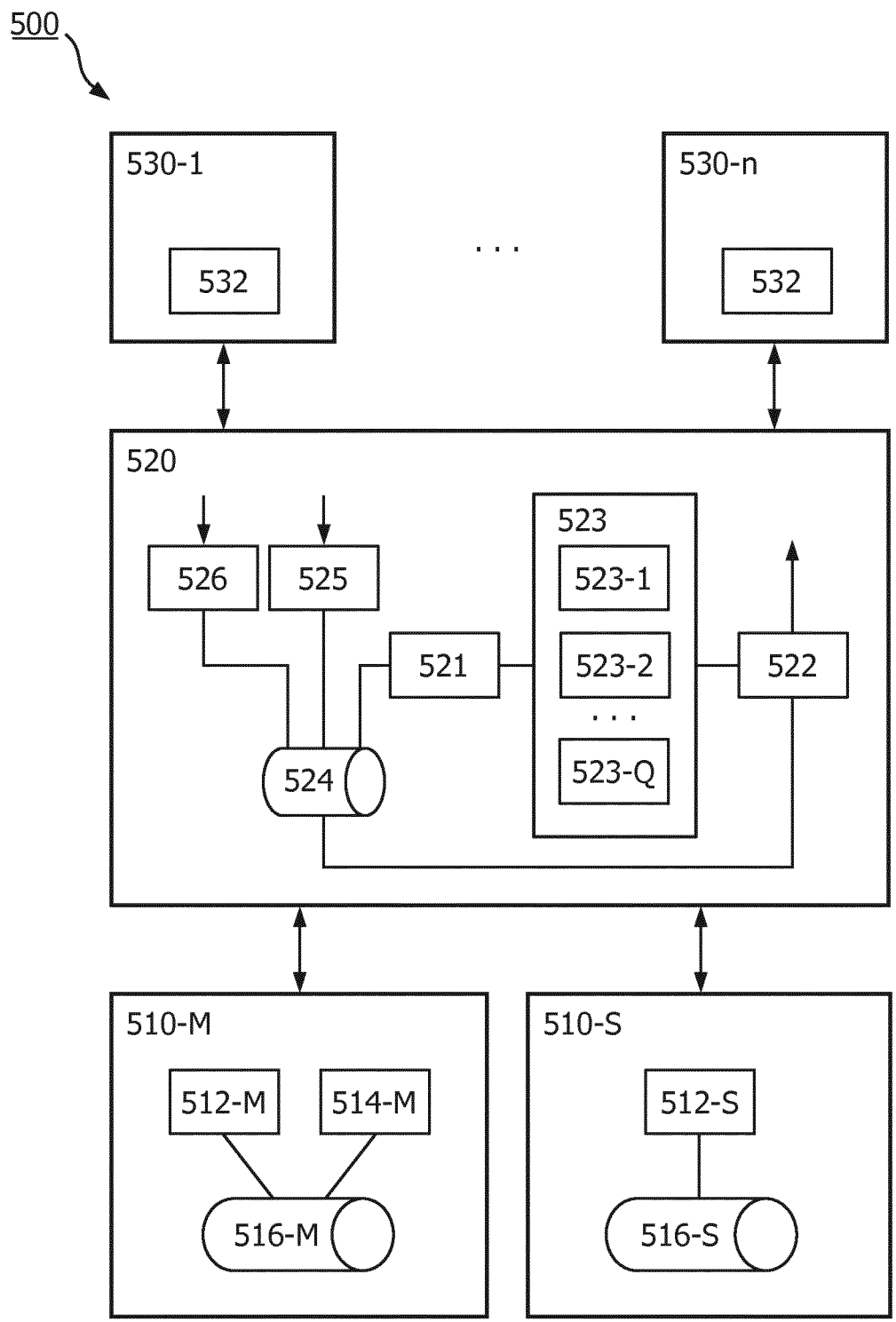
FIG. 5 illustrates the protocol module, network module, and the service modules of a node in accordance with an embodiment of the present invention.
Figure 6:
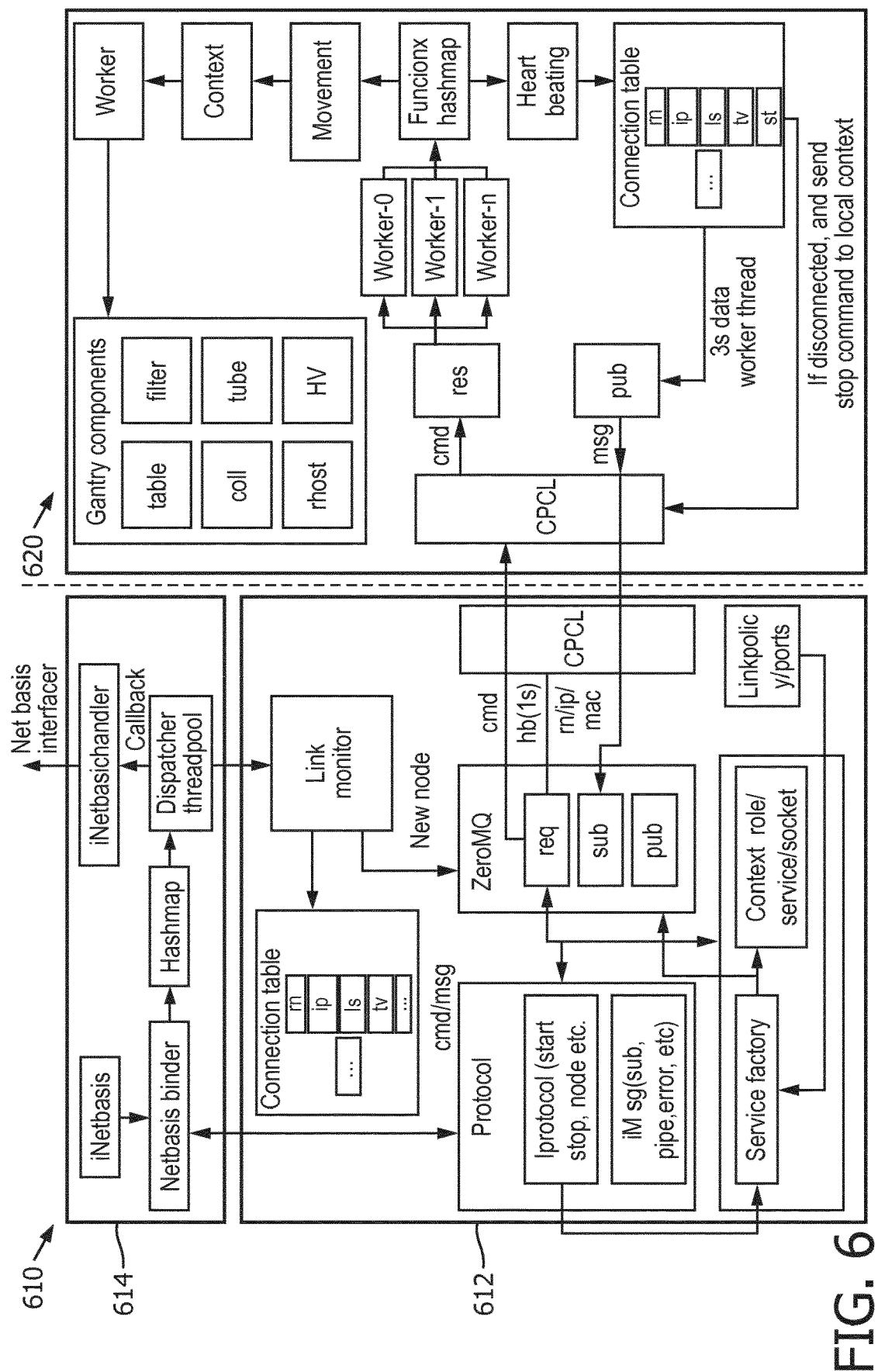
FIG. 6 illustrates an exemplary protocol module of a master node and an exemplary protocol module of a slave node in accordance with an embodiment of the present invention.

FIG. 5 illustrates the protocol module 510-M, 510-S, network module 520, and at least one service module 530-1, . . . , 530-*n* of a node 500 in accordance with an embodiment of the present invention. FIG. 4 illustrates an exemplary flow of establishing connections at the protocol layer in accordance with an embodiment of the present invention. FIG. 6 illustrates a protocol module 612 and a network module 614 of a slave node 610 and the interactions with a master node 620 in accordance with an embodiment of the present invention.

Referring to FIG. 5, each node 500 comprises a protocol module 510-M or 510-S depending on whether it is a master node or not, a network module 520 and one or more service modules 530-1 to 530-*n*.

The protocol module 510-M of the master node comprises a connection module 512-M and a memory 516-M. The protocol module 510-S of a slave node comprises a connection module 512-S and a memory 516-S.

The memory 516-M of the master node is configured to store connection information of one or more nodes. The connection information of a node comprises the node identifier, the node address, and the connection status of the node. The node identifier can be the name of the node or any value for uniquely identifying the node. The node address can be any address via which the node is accessible from the communication network. In an embodiment, the data structure "NodeInfo" for storing the connection information of a node can comprise an IP address "ipAddress", optionally an MAC address "MAC", a node identifier "roleType", the connection status "isOnline", and optionally a time stamp "lastTime" for indicating the time of receiving the last connection control message from the node, as described below:

```
NodeInfo {
    required string        ipAddress      = 1;
    optional string        MAC            = 2;
    required RoleType      roleType       = 3;
    required bool          isOnline       = 5;
    optional int64         lastTime       = 6;
}
enum RoleType { LEFT_PANEL = 1; RIGHT_PANEL = 2; CTBOX = 3; GANTRY = 4; CONSOLE = 5; ALL_NODES = 6;}
```

The connection module 512-M of the master node is configured to receive, from a node, a connection control message. The connection control message comprises the node address and the node identifier of the node. The connection module 512-M of the master node is configured to update the connection information based on the received connection control message. The connection module 512-M of the master node is further configured to generate a connection table based on the connection information, and to publish the connection table to all nodes, preferably at a pre-determined time interval, e.g. every 3 seconds. In an example, the connection table may indicate a mapping between the node identifier and the node address of all online nodes. In another example, the connection table may indicate a mapping between the node identifier, the node address, and the online status of all nodes. Once it has received the connection table from the master node, each slave node is able to establish a connection between itself and a node in the connection table by using the node address therein. Additionally, the slave node can be further configured to check the online status of a node, and if a node goes offline, to take one or more predetermined actions. In accordance with an embodiment, the connection module 512-S of a slave node is configured to send a connection control message. The connection control message can be periodically, e.g. every 1 second, sent by the slave node so as to timely inform the master node of its status, such as a change of its node address. The connection module 512-S of the slave node is further configured to receive, from the master node, the connection table, and to establish a connection to each of one or more nodes based on the connection table. The memory 516-S of the slave node can be configured to store its own node identifier, its own node address, and the established connections.

In some embodiments, the protocol module 510-M of the master node may further comprise a disconnection event handling module 514-M. The connection module 512-M of the master node is further configured to generate a disconnection event when a connection status of a node becomes disconnected based on the stored connection information, and to send the disconnection event to the disconnection event handling module 514-M. The memory 516-M of the master node is further configured to store a third mapping between the disconnection event and the at least one operation. The disconnection event handling module 514-M is configured to receive a disconnection event and to perform at least one operation in response to the disconnection event based on the third mapping.

Next, with reference to FIG. 4, the protocol module of a master node 410, the protocol module of a slave node 420 and the interconnection therebetween in accordance with an embodiment are described.

In step 422, the slave node 420 sends a connection control message 432 to the master node 410. Once it has received the connection control message 432 from the slave node 420, the master node 410 updates, in step 412, the stored connection information 440. The connection information 440 can be stored in a hash map. In particular, in step 4120, the master node 410 checks whether the node 420 exists in the stored connection information. If the node 420 does not exist in the stored connection information 440, such as a new node not previously known to the master node 410, the master node 420 can, in step 4122, create a new entry for the slave node 410 in the stored hash map 440 based on the received connection control message, including storing the node identifier, the node address of the node from the connection control message 432, and optionally the receiving time of the connection control message 432. If the node 420 already exists in the stored connection information such as the hash map 440, the master node 420 can, in step 4124, update the entry for the node 420 based on the connection control message, such as updating the node address if there is a change, and recording the receiving time of the connection control message 432. Once it has received a connection control message from a slave node, the master node 420 sets the status of the slave node as online, e.g. setting isOnline as true.

The master node 410 can be configured to publish a connection table 434. The connection table 434 can comprise the third mapping of node identifiers and node addresses for all online nodes. Upon receiving the connection table 434, the slave node 420 can, in step 424, establish or re-establish one or more connections based on the connection table. In particular, in step 4240, the slave node 420 can check whether or not a connection between itself and an online node has already been established. If not, the slave node 420 can establish a connection between itself and the online node based on the node identifier and node address of that online node, for example, for calling a method "nodeEnter (NodeInfo node)". The protocol module of the slave node can be configured to establish a connection by the port and service configuration when the method "nodeEnter (NodeInfo node)" is called.

Referring to FIG. 4, the master node 410 can be further configured to monitor, in step 414, the connection status of each node. In an embodiment, the master node 420 may set the status of the slave node to offline, e.g. setting isOnline is set to false, if it does not receive any connection control message from a slave node over a predetermined time period. Once it is detected, in step 4140, that a connection status of a node has become offline, the master node 420 generates a disconnection event and performs, in step 4142, at least one operation in response to the disconnection event. For example, when a slave is offline, the movement of the support might be dangerous, and must be stopped as soon as possible.

Additionally, the disconnection event can be generated by other means, such as by monitoring the status of the physical link. For example, a ZeroMQ network monitor can be used to check, in step 4144, the socket connection, so as to make full use of network idle, and send a disconnection event upon detecting a disconnection of an established connection.

The protocol module 510-M, 510-S of a node is further configured to send and receive a data message over the network. In some embodiments, the protocol module 510-M, 510-S of a node can be configured to send a data message by means of one of the following two methods, namely "ireq ( )" and "ipub ( )". The method "ireq ( )" is used to send a message which requires a response, and the method "ipub ( )" is used to send a message to one or more nodes and no response is required. Once a data message has been received, the protocol layer will deliver the data field of the received data message to the network module 520, and in some embodiments, to the dispatcher 521 of the network module 520.

In accordance with an embodiment of the present invention, the interface of the protocol module 510 is defined as follows:

```
public interface IMessageHandler{
    void pipeChanged(byte[ ] data);
    void dataChanged(byte[ ] data);
}
public interface IMessage {
    void    register(IMessageHandler sink);
    void    unregister(IMessageHandler sink);
    void    start( );
    void    stop( );
    void    nodeEnter(NodeInfo node);
    byte[ ] ireq(int roleType, byte[ ] msg);
    void    ipub(int roleType, byte[ ] msg);
}
```

Referring back to FIG. 5, the network module 520 comprises a dispatcher 521, a plurality of queues 523, a call-back module 522 and a memory 524. The memory 524 stores a first mapping between the message identifiers and the plurality of queues and a second mapping between the message identifiers MsgID and call-back handlers. The dispatcher 521 is configured to dispatch the data message to one of the plurality of queues 523 based on the message identifier MsgID and the first mapping, and the call-back module 522 is configured to process a data message in each of the plurality of queues based on the second mapping. Each call-back handler is directed to a message handler at a service module. The plurality of queues 523 can be created during the initialization, and/or can be dynamically created. In accordance with some embodiments, the mapping between queues and the message identifiers can be one-to-one or one-to-more, and the mapping between the call-back handlers and the message identifier is one-to-one.

In accordance with an embodiment of the present invention, the pseudo-code of the dispatcher 521 can be described as below:

```
public void dispatch(byte[ ] data) {
try {
Parse the message object from "byte[ ] data", for high performance the
message is based on protocol buffer(open source code library);
Get the queue name from queue hash map by message id.
Get the thread pool object by queue name by hash map.
Create a task object and call the thread pool to handle message content in
parallel.
    }
```

In accordance with some embodiments, one or more message identifiers are mapped to one of the plurality of queues. In other words, one or more types of data messages are grouped in a message group, and data messages of the same message group are dispatched to the same queue. Table 1 illustrates an exemplary first mapping. Five message groups are illustrated in Table 1, but more or fewer message groups can be defined as needed in other embodiments.

TABLE 1

An exemplary first mapping between MsgIDs and Queues

| Index | Queue name | Message group | Types of data messages |
|---|---|---|---|
| 1 | movement_pf | Position feedback | Messages carrying current gantry position, current tilt angle, subject support position, etc. |
| 2 | movement_ecg | ECG data | Messages carrying ECG data |
| 3 | movement_cmd | Movement command | Messages carrying target tilting angle, target vertical/horizontal position of subject support etc. |
| 4 | workflow_wf | Workflow command | Messages for patient register, orientation selection, exam card selection, etc. |
| 5 | workflow_patientslist | Patient list sync | Message for carrying the patient list |

One message group "Movement commands" is for the types of messages carrying movement commands, including, for example, a type of message for carrying the target tilting angle of the gantry, a type of message for carrying the target horizontal position and/or target vertical position of the subject support, etc. All messages in this group are dispatched to the queue "movement_cmd". One message group "Position feedback" is for the types of message carrying position feedback, including, for example, a type of message for carrying the current position of the gantry 104 such as the current tilting angle, a type of message for carrying the current position of the subject support 108, etc. All messages in this group are dispatched to the queue "movement_pf". One message group "ECG data" is for the types of messages carrying ECG data. All messages in this group are dispatched to the queue "movement_ecg". One message group "Workflow command" is for the types of messages carrying workflow command, including, for example, a type of message for patient register, a type of message for orientation selection, a type of message for exam card selection, etc. All messages in this group are dispatched to the queue "workflow_wf". One message group "Patient list" is for the types of message carrying a patient list. All messages in this group are dispatched to the queue "workflow_patient list".

Different queues may use different scheduling strategies, different queuing/de-queuing policies, and/or different number of threads. In an embodiment, for queue "movement_pf", the messages in the queue shall be handled in real time. That is, the call-back module 522 shall call the corresponding call-back handler to handle the messages in real time. However, since the latest message carries the most update position feedback, only the latest message needs to be handled whilst the previous ones can be dropped. In an embodiment, for queue "movement_ecg", the messages in the queue are handled one after another in real time, and no messages are dropped, because a complete set of ECG data is required. In an example, the messages to be dropped are dropped by the network module, and alternatively, the messages to be dropped can be passed to the service layer or the application layer and then dropped there. In an embodiment, for each of queue "movement_ms" and queue "workflow_wf", messages need to be handled in a synchronized manner by a single thread so as to avoid conflicts among the messages. For example, if a movement command, such as horizontally moving the subject support, comes when a same type of movement command is running, the latter command shall not be executed until the former command is completed. In an embodiment, for queue "workflow_patient list", messages shall be handled in a separate task queue without being shared with other types of messages because the amount of data is large and it requires a relatively long time to handle.

The network module 520 can further comprise a register 525. The register 525 is configured to receive, from the service module, a message identifier MsgID, a queue identity value for indicating one of the plurality of queues to which the data message with the message identifier is to be routed, and a call-back handler directed to a message handler for handling the data message with the message identifier, and to update the first mapping and the second mapping based on the received message identifier, the queue identity value and the call-back handler. In particular, a new entry can be created in the first mapping so as to create a mapping between the message identifier and the queue identity value, and a new entry can be created in the second mapping so as to create a mapping between the message identifier and the call-back handler. In some embodiments where the plurality of queues 523 can be dynamically created, the register unit 525 can be further configured to check whether a queue with the received queue name exists or not, and if not, to create a queue with the received queue name.

In accordance with an embodiment of the present invention, the pseudo-code of the register 525 can be described as below:

```
        public void register(int msgID, String queueName,
INetBasisCallback callback) {
            if (callback == null || queueName == null)
                return;
Create the map between queue name and message id.
Create the map between message id and callback.
//if the hash map between queue name and thread pool is already exists,
//and just uses it, otherwise create it.
Create the map between thread pool and queue name.
        }
```

In some embodiments, the register 525 may be further configured to set the number of thread pools for a queue. In an example, the number of thread pools for a queue can be set to one, if the data message in the queue can (?) be handled in a synchronized manner. In another example, the number of thread pools for a queue can be set to more than one, if the data message in the queue can be handled asynchronously. In this case, the register 525 is further configured to receive, from the service module 530, a value for indicating the number of thread pools assigned to the queue, for example by means of following method: void register (int msgID, String queueName, int threadNumber, INetBasisCallback callback);

The network module 520 can further comprise an unregister 526. The unregister 526 is configured to receive, from the service module, a message identifier MsgID, and to update the first mapping and the second mapping based on the received message identifier. In particular, the mapping related to the received message identifier is removed from the first and second mapping. By means of calling the register 525, the service module can add a message of interest; by means of calling the unregister 526, the service module can remove a message which is not of interest anymore. Thus, the service module is able to dynamically modify its messages of interest without the need to change any source code.

In accordance with an embodiment of the present invention, the pseudo-code of the unregister 526 can be described as below:

```
    public void unRegister(int msgID) {
        Get the queue name via message id from their map;
        Remove the map between message id and queue name;
        Get the thread pool from map of queue name and thread pool;
        Shutdown the thread pool and remove the map node;
        Remove that map between call back and message id;
    }
```

Figure 7:
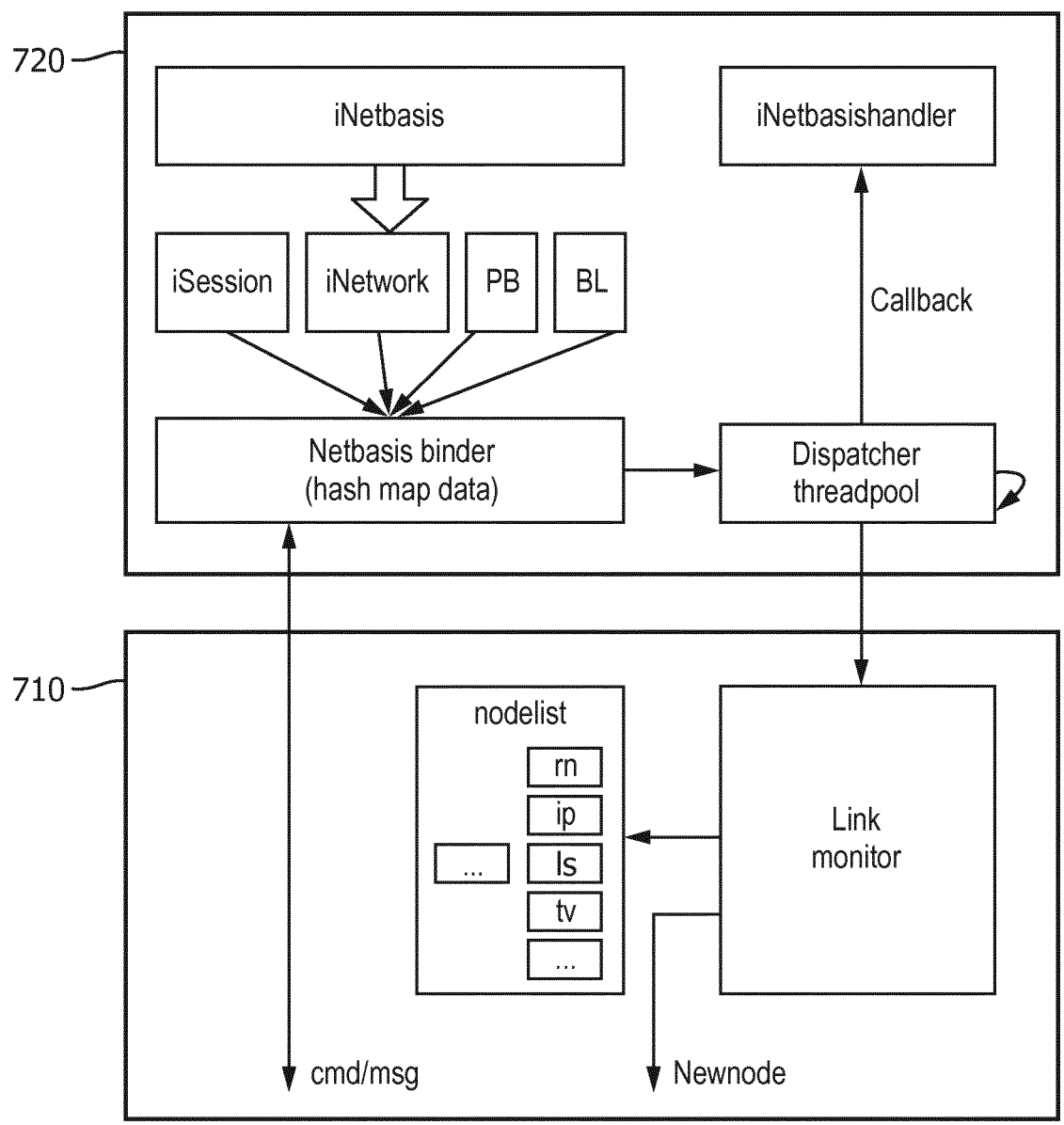
FIG. 7 illustrates the architecture of an exemplary network module and an exemplary protocol module in accordance with an embodiment of the present invention.

FIG. 7 illustrates the architecture of an exemplary network module 720 and an exemplary protocol module 710 in accordance with an embodiment of the present invention. Referring to FIG. 7, in the bottom-up direction, the network module 720 receives messages from a lower layer, namely the protocol layer 710, dispatches the received messages, and then passes the received messages to be handled by the higher layer, namely the service layer, via the call-back handlers. In the top-down direction, the network module 700 receives messages from a higher layer, namely the service layer, various types of messages to be sent to other nodes, and sends these messages to the protocol layer 710. The messages received from the service layer may comprise messages for various services, such as iSession, iNetwork, PB (position beam), BL (beam limitation).

In accordance with an embodiment of the present invention, the interface of the network module can be defined as follows:

```
interface INetBasis {
    void start( );
    void stop( );
    void unRegister(int msgID);
    void register(int msgID, String queueName, INetBasisCallback
callback);
    byte[ ] ireq(int roleType, in byte[ ] data);
    void ipub(int roleType, in byte[ ] data);
}
interface INetBasisHandler {
    void invoke(in byte[ ] data);
}
```

Referring back to FIG. 5, the node 500 may comprise at least one service module 530-1, . . . , 530-n. Each service module comprises at least one message handler 532 for handling a payload of a data message. Each message handler 532 can be called by the network module by means of the corresponding call-back handler which is directed to the enter address of the message handler 532.

Figure 8:
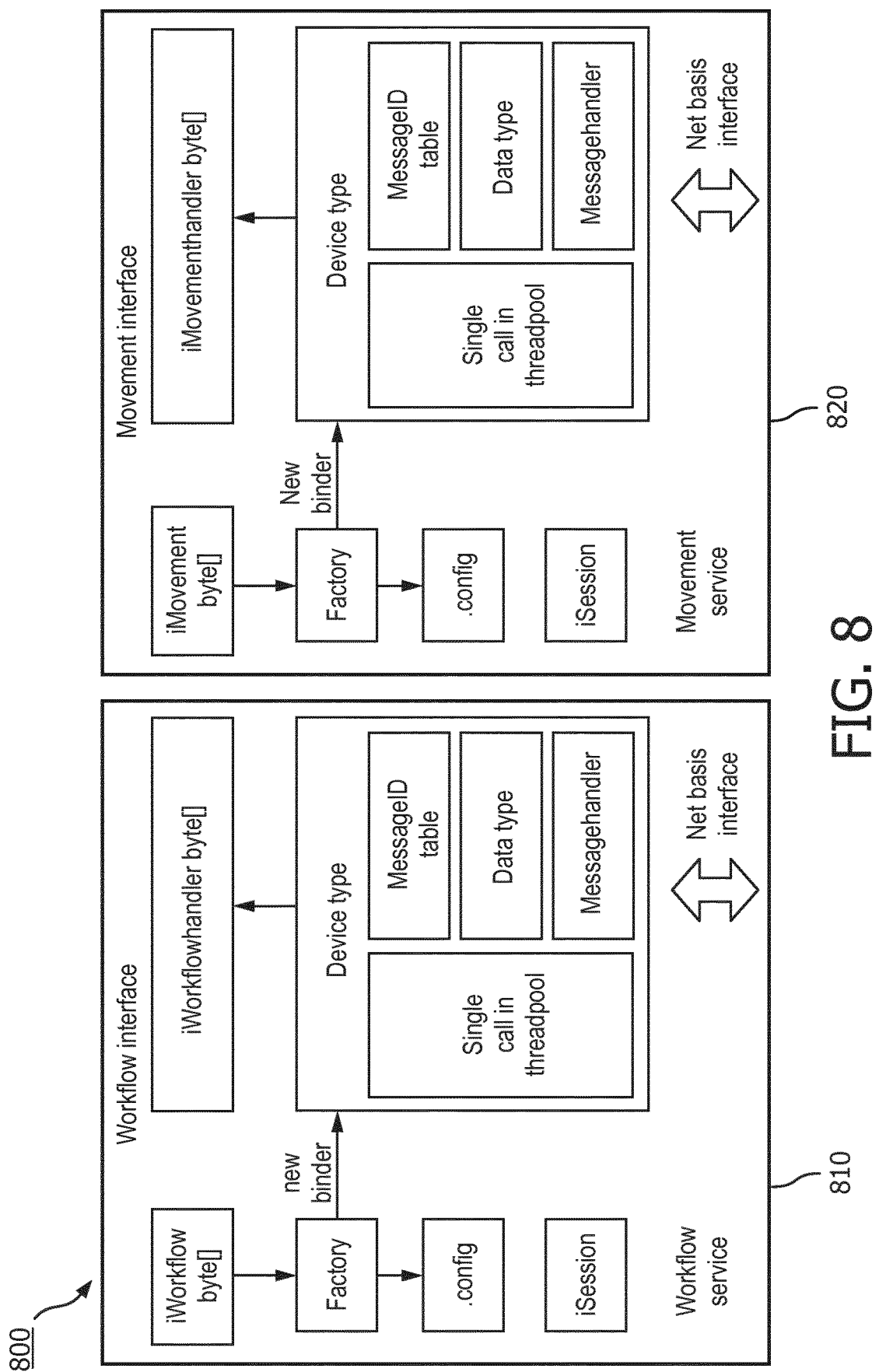
FIG. 8 illustrates the architecture of an exemplary service layer comprising at least one service module in accordance with an embodiment of the present invention.
Figure 9:
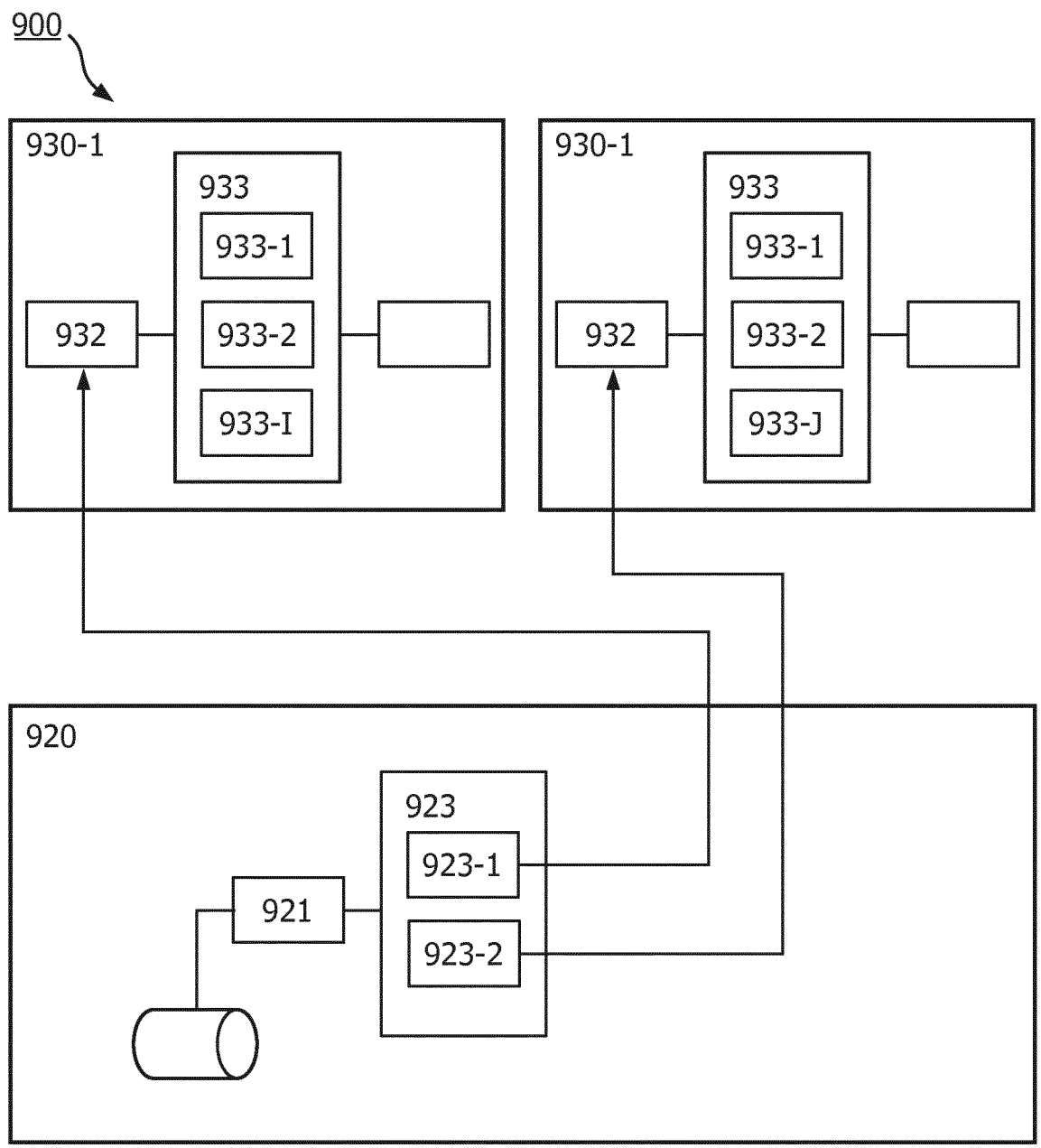
FIG. 9 illustrates the protocol layer, network layer, and the service layer of a node in accordance with another possible solution.

FIG. 8 illustrates the architecture of an exemplary service layer 800 comprising at least one service module in accordance with an embodiment of the present invention. Two service modules, namely one service module 810 for workflow service and the other service module 820 for movement service, are illustrated in FIG. 8, but more or fewer service modules can be configured. In accordance with an embodiment, the service modules can be implemented via remote service components in Android or COM components in Microsoft Windows or any other suitable operation systems.

In some embodiments, a service module can be configured to handle messages of a single service or to handle messages of multiple services. For example, the service for controlling beam position and the service for beam limitation are both provided by the same node, namely the gantry host, and therefore messages for these two services can be designed to be handled at one service module.

In some embodiments, a service is provided or executed by one node, but can be accessed by more than one node. For example, the service for controlling scan flow is provided by the console, but can be accessed by different nodes such as a left panel, a right panel and an operation box. The service module of the different nodes for accessing the same service can be the same or different. In an embodiment, among the service modules of the different nodes for accessing the same service, the message ID table can be the same, the date type can be the same, but the message handler for handling the same type of message can be different.

Message handlers of the service modules are responsible for processing the messages and passing the messages to the upper layer, such as the application layer. In some embodiments, the message handler can be configured to pass one message to more than one applications at the application layer.

Figure 10:
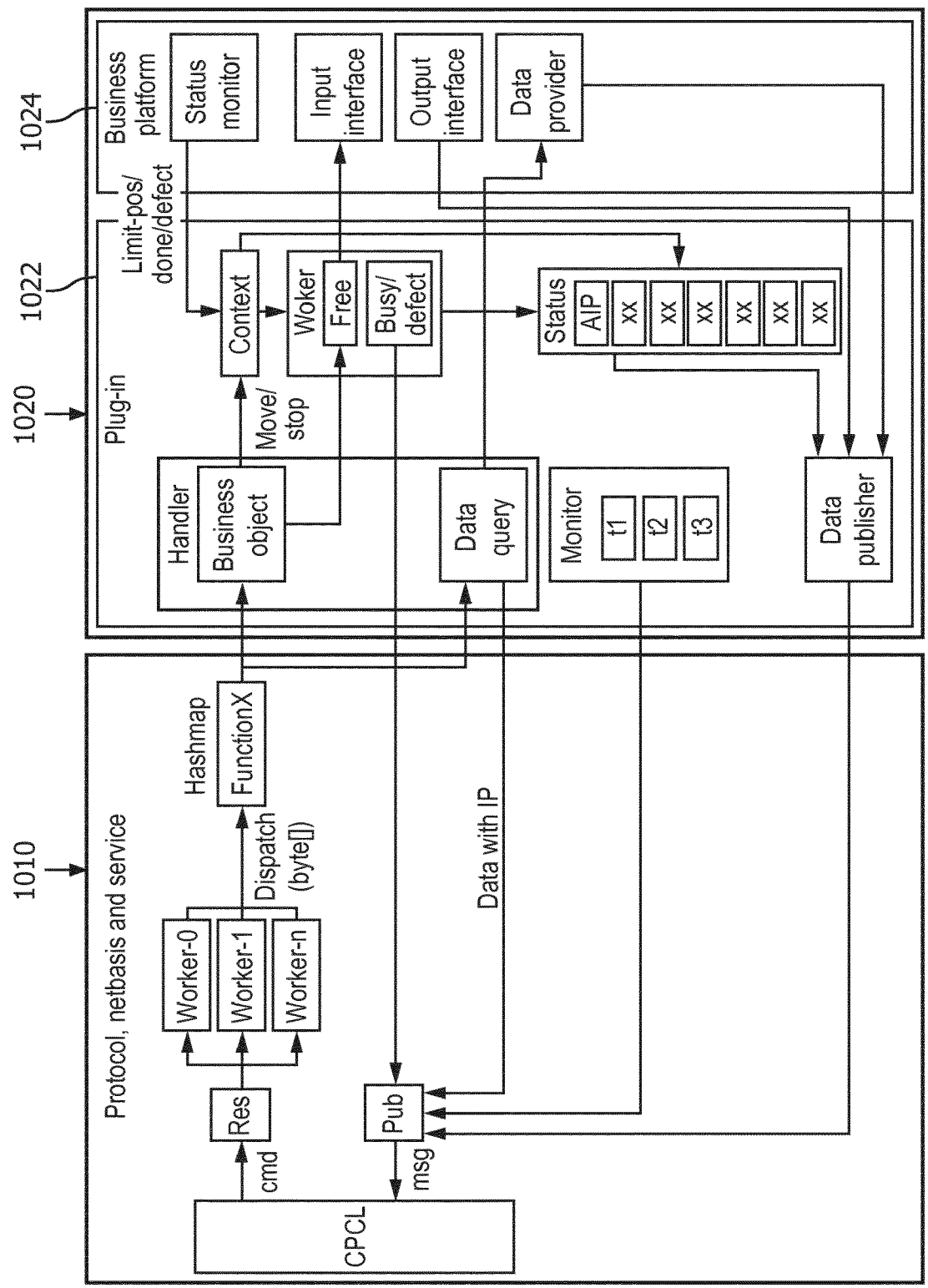
FIG. 10 illustrates the architecture of an exemplary node for providing services, such as a gantry host or a console, in accordance with an embodiment of the present invention.

FIG. 10 illustrates the software architecture of an exemplary node for providing services, such as a gantry host or a console, in accordance with an embodiment of the present invention. The illustrated architecture comprises the protocol, network and service layers 1010 and the application layer 1020. The application layer 1020 comprises a business platform 1024 for providing services, and a plug-in 1022 for allowing other nodes to access its provided services.

In some embodiments, some of the plurality of nodes are configured to provide services (called business node hereafter), such as the console and the gantry host. The business nodes mainly serve as a response server and a publish server. Referring to FIG. 10, for a business node, it mainly receives messages via interface "res ( )", and sends messages via interface "pub ( )". The response server should be implemented by a multi-worker mode; the service provider will register the commands of interest and handle them in parallel.

Referring to FIG. 10, the plug-in 1022 can comprise a command handler, a state machine, some status tables, a status monitor and a data publisher.

The status tables for different nodes can be different. For example, in a gantry host which provides movement control service, the status tables can comprise status values for movement axis, status values for connections, and/or status values for position feedback. For example, in a console which provides workflow service, the status tables can comprise status values for the scan flow.

The monitor is a thread which will start a timer to update all status tables to its slave nodes for a predetermined time interval, such as every 3 seconds. In a gantry host, the monitor can be further configured to check the online status of a physical connection, and to stop on-going movement if a certain connection becomes offline. In a console, the monitor can ensure that procedure data will be published timely.

The technique processes described herein may be implemented by various means. For example, these techniques may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. With software, implementation can be through modules (e.g., procedures, functions, and so on) that perform the functions described herein. The software codes may be stored in a memory unit and executed by the processors.

Moreover, aspects of the claimed subject matter may be implemented as a method, apparatus, system, or article of manufacture using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope or spirit of what is described herein.

As used in this application, the terms "module" such as protocol module, network module, service module, callback module, connection module, disconnection event handling module, "dispatcher", "queue", "register", "unregister", "estimator" such as "shear wave detector", "property estimator" and "imaging encoder" are intended to refer to a processor or a computer-related entity, either hardware, a combination of hardware and software, software, or software in execution, but in particular they refer to software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. A node of a plurality of nodes in an imaging system, the imaging system comprising a network for communication among the plurality of nodes in the imaging system, the node comprising:
processor circuitry configured to:
receive a data message over the network; and
receive a data field of the data message, wherein
the data field comprises a message identifier for indicating a type of the data message, and a payload field;
wherein the processor circuitry is further configured to handle a payload of a data message;
wherein the node comprises a memory configured to store:
a first mapping between the message identifiers and a plurality of queues; and
a second mapping between the message identifiers and call-back handlers;
wherein the processor circuitry is further configured to dispatch the data message to one of the plurality of queues based on the message identifier and the first mapping;
wherein the processor circuitry is further configured to process a data message in each of the plurality of queues based on the second mapping, each of the call-back handlers being directed to a message handler; and
wherein the plurality of queues comprises a first queue and a second queue, and the number of threads assigned to the first queue is different from the number of threads assigned to the second queue.

2. The node of claim 1, wherein the processor circuitry is further configured to:
receive the message identifier, a queue identity value for indicating one of the plurality of queues to which the data message with the message identifier is to be dispatched and a call-back handler directed to a message handler for handling the data message with the message identifier;
update the first mapping and the second mapping based on the received message identifier, the received queue identity value, and the received call-back handler.

3. The node of claim 2, wherein the processor circuitry is further configured to generate the message identifier, a queue identity value for indicating one of the plurality of queues to which the data message with the message identifier is to be dispatched, and a call-back handler directed to a message handler for handling the data message with the message identifier based on configuration data.

4. The node of claim 2, wherein the processor circuitry is further configured to:
receive the message identifier; and
update the first mapping and the second mapping based on the received message identifier by removing the mapping corresponding to the received message identifier.

5. The node of claim 1, wherein the processor circuitry is further configured to send a value for indicating a number of threads assigned for a queue of the plurality of queues.

6. The node of claim 1, wherein one or more message identifiers are mapped to one of the plurality of queues.

7. The node of claim 1, wherein
the processor circuitry is further configured to send the data field and a node identifier, the node identifier indicating one or more nodes to which the data field is sent; and the processor circuitry is further configured to generate the data message based on the data field and the node identifier.

8. The node of claim 1, wherein
the plurality of nodes comprises a master node and at least one slave node;
the memory of the master node is configured to store connection information of one or more nodes, and the connection information of a node comprises the node identifier, the node address, and the connection status of the node;
the master node is configured to receive, from a node, a connection control message, the connection control message comprising:
a node address of the node, the node address being unique in the network and being dynamically defined;
a node identifier of the node, the node identifier being unique in the network;
the master node is further configured to update the connection information based on the received connection control message, and to send out a connection table based on the connection information, the connection table indicating a mapping between the node identifier and the node address.

9. The node of claim 8, wherein the master node is a gantry host.

10. The node of claim 8, wherein
the master node is further configured to generate a disconnection event when a connection status of a node becomes disconnected based on the stored connection information, and to send the disconnection event;
the memory of the master node is further configured to store a third mapping between the disconnection event and the at least one operation; and
the master node is configured to receive a disconnection event and to perform at least one operation in response to the disconnection event based on the third mapping.

11. The node of claim 8, wherein
one of the at least one slave node is configured to send a connection control message;
the one of the at least one slave node is further configured to receive, from the master node, the connection table, and to establish a connection to each of one or more nodes based on the connection table.

12. The node of claim 1, wherein the processor circuitry is configured to receive the data message over the network by cross-platform.

13. An imaging system, comprising:
a plurality of nodes; and
a network for communication among the plurality of nodes,
wherein one of the plurality of nodes comprises:
processor circuitry configured to:
receive a data message over the network; and
receive a data field of the data message,
wherein the data field comprises a message identifier for indicating a type of the data message, and a payload field;
wherein the processor circuitry is further configured to handle a payload of a data message;
wherein the node comprises a memory configured to store:

a first mapping between the message identifiers and a plurality of queues; and a second mapping between the message identifiers and call-back handlers;

wherein the processor circuitry is further configured to dispatch the data message to one of the plurality of queues based on the message identifier and the first mapping;

wherein the processor circuitry is further configured to process a data message in each of the plurality of queues based on the second mapping, each of the call-back handlers being directed to a message handler; and wherein the plurality of queues comprises a first queue and a second queue, and the number of threads assigned to the first queue is different from the number of threads assigned to the second queue.

14. A non-transitory computer-readable medium comprising a computer program product including program code instructions recorded thereon, the computer program product configured for execution by computer circuitry, wherein the computer program product when executed by the computer circuitry performing a method of communication among a plurality of nodes in an imaging system over a network, the method comprising:

at a protocol layer, receiving a data message over the network;

at a network layer, receiving a data field of the data message, the data field comprising a message identifier for indicating the type of message, and a payload field;

dispatching the data message to one of a plurality of queues based on the message identifier and a first mapping between the message identifiers and the plurality of queues;

processing a data message in each of the plurality of queues based on a second mapping between the message identifier and a call-back handler, each call-back handler being directed to a message handler at a service layer for handling the payload of the data message; and at the service layer, handling the payload of the data message; and wherein the plurality of queues comprises a first queue and a second queue, and the number of threads assigned to the first queue is different from the number of threads assigned to the second queue.

* * * * *